United States Patent
Chopdekar et al.

(10) Patent No.: US 7,662,802 B2
(45) Date of Patent: Feb. 16, 2010

(54) HALIDE-FREE GLUCOSAMINE-ACIDIC DRUG COMPLEXES

(75) Inventors: Vilas M. Chopdekar, Edison, NJ (US); Michael J. Torntore, Edison, NJ (US)

(73) Assignee: Gluconova, LLC, Wilmington, DE (US)

( * ) Notice: Subject to any disclaimer, the term of this patent is extended or adjusted under 35 U.S.C. 154(b) by 344 days.

(21) Appl. No.: 11/731,294

(22) Filed: Mar. 31, 2007

(65) Prior Publication Data

US 2007/0249735 A1    Oct. 25, 2007

Related U.S. Application Data

(63) Continuation-in-part of application No. 11/223,686, filed on Sep. 9, 2005.

(60) Provisional application No. 60/611,178, filed on Sep. 17, 2004.

(51) Int. Cl.
| | |
|---|---|
| A01N 43/04 | (2006.01) |
| A01N 43/08 | (2006.01) |
| C07H 5/04 | (2006.01) |
| C07H 5/06 | (2006.01) |
| C07H 17/04 | (2006.01) |

(52) U.S. Cl. .......... 514/62; 536/55.2; 536/17.2
(58) Field of Classification Search ............ None
See application file for complete search history.

(56) References Cited

U.S. PATENT DOCUMENTS

| | | | | |
|---|---|---|---|---|
| 3,008,874 | A | 11/1961 | Feeney et al. | 167/55 |
| 4,748,174 | A | 5/1988 | Veronesi | 514/226.5 |
| 4,877,620 | A | 10/1989 | Loew et al. | 424/451 |
| 5,028,625 | A | 7/1991 | Motola et al. | 514/557 |
| 5,604,206 | A | 2/1997 | Paradies | 514/23 |
| 6,291,527 | B1 | 9/2001 | Giorgetti | 514/570 |
| 6,294,520 | B1* | 9/2001 | Naito | 514/23 |
| 6,486,307 | B1 | 11/2002 | Gandhi et al. | 536/20 |
| 6,608,041 | B2 | 8/2003 | Hammerly | 514/54 |
| 6,900,189 | B2* | 5/2005 | Raffa et al. | 514/62 |
| 6,962,717 | B1* | 11/2005 | Huber et al. | 424/490 |
| 2002/0058642 | A1 | 5/2002 | Raffa et al. | 514/62 |
| 2003/0148998 | A1 | 8/2003 | Fan et al. | |
| 2004/0077055 | A1 | 4/2004 | Fosdick et al. | 435/85 |
| 2004/0091976 | A1 | 5/2004 | Deng et al. | 435/84 |
| 2005/0148545 | A1 | 7/2005 | Fosdick et al. | 514/62 |
| 2005/0148546 | A1 | 7/2005 | Grund et al. | 514/62 |

OTHER PUBLICATIONS

Drug Development and Industrial Pharmacy, 25(8), 967-972 (1999).

* cited by examiner

*Primary Examiner*—Ardin Marschel
*Assistant Examiner*—Amy A Lewis
(74) *Attorney, Agent, or Firm*—Jack Matalon

(57) ABSTRACT

A complex of glucosamine having a purity of at least about 99 wt. % and a maximum halide content of about 0.01 wt. %, and a therapeutic drug having a $pK_a$ of less than 7. Preferably, the complex is stabilized by coating it with at least one pharmaceutically acceptable polymer comprising a water-soluble, water-immiscible and/or water-swellable homopolymer and/or copolymer. Suitable polymers include carboxypolymethylene homopolymers and copolymers; polyethylene glycol homopolymers and copolymers, povidone homopolymers and copolymers; polyacrylic acid homopolymers and copolymers; polyacrylamide homopolymers and copolymers; polysaccharides; and mixtures of two or more of the foregoing polymers. The resultant coated complex will be stable upon exposure to ambient temperature and/or the atmosphere. Suitable therapeutic drugs fall into the following classes: α- and β-Adrenergic Agonists; Narcotic and Non-Narcotic Analgesics; Anorexics; Antiallergics; Antianginals; Antiarrhythmics; Antiasthmatics; Antibiotics; Anticoagulants; Anticonvulsants; Antidepressants; Antidiabetics; Antihistaminics; Antihypertensives; Nonsteroidal Anti-Inflammatories; Antimigraines; Antineoplastics; Antiparkinsonians; Antipsychotics; Antipyretics; Antispasmodics; Antithrombotics; Antiulceratives; Anxiolytics; Decongestants; Diuretics; Hepatoprotectants; Sedatives; and Vasodilators.

23 Claims, No Drawings

HALIDE-FREE GLUCOSAMINE-ACIDIC DRUG COMPLEXES

CROSS-REFERENCE TO RELATED APPLICATIONS

This application is a continuation-in-part of application Ser. No. 11/223,686 filed Sep. 9, 2005 which in turn claimed the benefit of provisional application Ser. No. 60/611,178 filed Sep. 17, 2004.

FIELD OF THE INVENTION

The invention relates to halide-free glucosamine complexes of acidic drugs and to methods for preparing such complexes.

BACKGROUND OF THE INVENTION

Glucosamine is a well-known amino monosaccharide found in chitin. glycoproteins and glycosaminoglycans. Glucosamine is widely used for the treatment of rheumatic fever, arthritic and arthosic complaints, in the acute as well as chronic forms, as well as in the treatment of pathological conditions originating from metabolic disorders of the osteo-articular tissue. Although products in the marketplace are labeled as, or referred to as, "glucosamine", they are misnomers since such products consist of glucosamine hydrochloride or as unreacted mixtures of glucosamine hydrochloride and a complex such as potassium or sodium sulfate.

One drawback of many therapeutic drugs is their relative insolubility in the body after they have been administered to a patient. It would be most desirable if more soluble versions of therapeutic drugs could be made available.

It has now been found that complexes of halide-free glucosamine and acidic drugs are more soluble than the drugs themselves. An added benefit is that glucosamine itself is formed in the body (typically in the form of glucosaine phosphate) and therefore no "foreign" ingredients will be introduced in the body when the complexes of the invention are administered to patients in need of such drugs.

Salts or mixtures of "glucosamine" or "glucosamine sulfate" and a therapeutic drug such as aspirin, ibuprofen, ketoprofen, etc. are known in the prior art, e.g., see U.S. Patent Publication 2002/0058642 A1; U.S. Pat. Nos.6,608,041 B2; U.S. Pat. Nos. 6,291,527 B1; U.S. Pat. Nos. 5,604,206; and U.S. Pat. Nos. 3,008,874. However, the "glucosamine" or "glucosamine sulfate" employed in such compositions are misnomers, inasmuch as such materials are actually glucosamine hydrochloride or mixed complexes of glucosamine hydrochloride and an alkali or alkaline earth metal sulfate.

In contradistinction thereto, the glucosamine employed in preparing the complexes of the invention is halide-free (i.e., the glucosamine has a purity of at least about 99 wt. % and a maximum halide content of about 0.01 wt. %) and as a result, the complexes of the invention will contain neither a halide nor any extraneous anions nor any extraneous cations (e.g., sodium, potassium, calcium, etc.).

DETAILS OF THE INVENTION

The starting materials for preparing the complexes of the invention are halide-free glucosamine and a therapeutic drug having a $pK_a$ of less than 7. Such drugs will contain at least one acid functionality, e.g., a carbonyl moiety, a carboxyl moiety and/or a sulfoxide moiety.

Glucosamine, extracted from shellfish or prepared by a fermentation process, is only available in the form of its hydrochloride salt. If the glucosamine hydrochloride salt is neutralized with a base, e.g., NaOH, KOH, etc. in order to release the glucosamine, the resultant product will always contain a salt, i.e., NaCl or KCl, respectively, and it is not possible to separate the glucosamine from the salt since both the glucosamine and the salt are fully soluble in water.

Free glucosamine be prepared by the method recited in *Chem. Ber.*, volume 75, page 1274. Such method involves the treatment of glucosamine hydrochloride with an ethanolic solution of a tertiary base such as triethylamine. Triethylamine hydrochloride is filtered off and the free glucosamine is then recovered from the reaction mixture. However, triethylamine is a toxic material even in small quantities and the yield of the free glucosamine is quite low. Moreover, the free glucosamine still contains residual chloride.

A method for producing halide-free glucosamine with a very high degree of purity has now been discovered. Such method is fully described in co-pending patent application Ser. No. 11/223,236 filed Sep. 9, 2005, which in turn claims the benefit of provisional application Ser. No. 60/611,709 filed Sep. 17, 2004. The aforesaid co-pending patent application is hereby incorporated herein in its entirety. By way of summary, the method disclosed in the aforesaid co-pending patent application is as follows:

(a) a glucosamine halide complex (e.g., glucosamine hydrochloride, glucosamine hydroiodide, etc.) is reacted with a lithium base in the presence of a $C_1$-$C_4$ alcohol to thereby generate a $C_1$-$C_4$ alcohol solution of a lithium halide and insoluble halide-free glucosamine; and (b) the insoluble halide-free glucosamine is separated from the $C_1$-$C_4$ alcohol solution of the lithium halide complex.

For maximum yields, the reaction should be carried out at a temperature of about 15 to about 35° C.; conveniently, the reaction may be carried out at ambient temperatures. The $C_1$-$C_4$ alcohol may be, e.g., methanol, ethanol (preferably anhydrous), isopropanol, etc; the preferred alcohol comprises methanol. The lithium base may be anhydrous lithium hydroxide, lithium hydroxide monohydrate, lithium methoxide, lithium ethoxide or lithium isopropoxide. The preferred lithium base comprises anhydrous lithium hydroxide. It has been found that the presence of water in the reaction mixture reduces the yield of the halide-free glucosamine. Accordingly, it is preferred that the reaction be carried out under anhydrous conditions. In general, the lithium base is employed in an amount of about 1.0 to about 1.2 moles per mole of halide present in the glucosamine halide complex. Excess lithium base is unnecessarily wasteful and will reduce the yield of the halide-free glucosamine. Typically, the alcohol is employed in an amount of about 1 to about 10 parts, preferably 3 to 6 parts, per part of lithium base.

After allowing the reaction to proceed (preferably with stirring) for about 5 minutes to about 2 hours, the solid halide-free glucosamine is filtered off from the resultant alcohol solution of the lithium halide and washed with additional alcohol. The halide-free glucosamine may then be dried under vacuum at a temperature of about 15 to about 30° C. The yield typically ranges from about 85 to about 90%. The halide-free glucosamine is quite pure. It will have a purity level of greater than about 99 wt. % and the halide content will be about 0.01 wt. % or less, e.g., 100 ppm or less and very often, the halide content will be less than 50 ppm and as low as 25 ppm. Based upon the residual halide content of the halide-free glucosamine, the lithium residue in the glucosamine will generally be about 20 ppm or less and very often, the lithium residue content will be less than 10 ppm The halide-free glucosamine is quite hygroscopic and will decompose over a period of time if subjected to ambient temperature and/or to the atmosphere. Accordingly, it should be refrigerated in a closed container or preferably promptly used after recovery for conversion to the complexes of the invention as described below.

The halide-free glucosamine may be readily converted to the glucosamine-acidic drug complex of the invention by reacting the glucosamine with a therapeutic drug having at least one acidic functionality, i.e. a therapeutic drug having a $pK_a$ of less than 7. The molar ratio of the halide-free glucosamine to the acidic drug in the complex is not critical and may be in the range of about 1 mole of glucosamine per mole of the drug up to about 15 moles of the glucosamine per mole of the drug. If the selected drug has more than one acidic functionality, the molar ratio of the glucosamine to the selected drug should be adjusted such that there will be about 1 to about 15 moles of glucosamine employed per acidic functionality in the selected drug.

Typically, the reaction mixture will comprise the halide-free glucosamine, about 5 to about 30 parts, preferably 15 to 20 parts, of water (preferably purified water) per part of the glucosamine and the selected drug. Although lesser amounts of water may be employed, the resultant solutions may become too viscous to be properly agitated, particularly if the glucosamine-therapeutic drug complex is not isolated from the reaction mixture, but is stabilized by the addition of a polymer to the reaction mixture, as described below. On the other hand, excessive amounts of water may lead to reduced yields if a water-miscible solvent is used to recover the complex and if freeze-drying is used to recover the complex, the freeze-drying process becomes more time-consuming and expensive because of the large amount of water to be removed from the reaction mixture.

The selected acidic drug is slowly added to the aqueous solution of the halide-free glucosamine while the aqueous solution is agitated, e.g. over a period of a few minutes, and the reaction mixture is further agitated for 5 to 120 minutes. The reaction is typically conducted at a temperature of about 15 to about 40° C. Thereafter, the glucosamine-acidic drug complex of the invention may be recovered from the reaction mixture by freeze-drying or by adding a water-miscible solvent such as acetone to the reaction mixture such that the complex will precipitate from the reaction mixture and the complex is then recovered by conventional filtration methods. The complex may then be dried by conventional methods, e.g., a stream of nitrogen, a vacuum oven at 30-50° C. for a period of 1 to 10 hours, etc. It is preferred that the recovery of the halide-free glucosamine-acidic drug complex of the invention be carried out by a freeze-drying process as described in greater detail below.

Some of the halide-free glucosamine-acidic drug complexes of the invention may decompose over a period of time if they are exposed to ambient temperatures or the atmosphere. Therefore, it is preferred that the complex not be recovered from the reaction mixture as is, but converted to a stabilized form prior to recovery. Conversion of the complex to its stabilized form may be desirable even for those complexes that do not decompose upon exposure to ambient temperatures and/or the atmosphere, since the pharmaceutically acceptable polymers employed in stabilizing, i.e., coating, the complexes of the invention may provide extended-release properties when the complexes are administered to warm-blooded vertebrates in need of treatment.

Stabilization of the halide-free glucosamine-acidic drug complex is readily accomplished by adding a suitable pharmaceutically acceptable polymer to the reaction mixture prior to recovery of the complex. The pharmaceutically acceptable polymer may be a water-soluble, water-dispersible and/or or a water-swellable homopolymer and/or copolymer. Preferably, the pharmaceutically acceptable polymer will be water-soluble. In general, the polymer will be employed in an amount of about 2 to about 70, preferably 20 to 50, parts by weight of the polymer per part of the complex in the reaction mixture.

Nonlimiting examples of commercially available pharmaceutically acceptable homopolymers and copolymers suitable for stabilizing the halide-free glucosamine-therapeutic drug complexes of the invention include the following: carboxypoly-methylene homopolymers and copolymers, i.e., vinyl polymers having active carboxyl groups such as high molecular weight homopolymers of acrylic acid crosslinked with allylsucrose or allylpentaerythritol and copolymers of acrylic acid modified by long chain ($C_{10}$-$C_{30}$) alkyl acrylates and crosslinked with allylpentaerythritol —such polymers are commercially available and are marketed as Carbopol® polymers; polyethylene glycol homopolymers and copolymers (e.g., polyethylene-co-lactic acid copolymers), particularly polyethylene glycol polymers having molecular weights in the range of about 2,000 to about 20,000, preferably 4,000 to 18,000; polypropylene glycol homopolymers and copolymers, especially polypropylene glycol homopolymers having molecular weights of about 800 to about 18,000; ethylcellulose; povidone homopolymers, i.e., synthetic water-soluble homopolymers of N-vinyl-pyrrolidone, especially those having a molecular weight of about 2,500 to about 10,000; copovidone, i.e. synthetic random copolymers of N-vinylpyrrolidone and vinyl acetate in a 60:40 ratio; polyacrylic acid homopolymers and copolymers; polyacrylamide homopolymers and copolymers; polysaccharides; etc.

The choice of particular homopolymers and/or copolymers for coating, i.e., stabilizing, the complex, is not critical so long as the polymers are pharmaceutically acceptable, have the capability of coating, i.e., stabilizing, the complex without any adverse chemical reaction occurring between the selected polymer and the complex and the resultant coated complexes are stable, i.e., they will not undergo decomposition when exposed to ambient temperatures and/or the atmosphere.

If the complex is to be recovered from the reaction mixture in a stabilized form, the desired pharmaceutically acceptable polymer is added, preferably in increments, with stirring, to the aqueous halide-free glucosamine solution preferably prior to the addition of the acidic drug. This step will generally take about 5 to about 15 minutes and is preferably conducted at a temperature of about 15 to about 40° C. After all increments of the selected polymer have been added, stirring is continued for an additional 5 to 120 minutes. Thereafter, the acidic drug is slowly added to the reaction mixture, while maintaining the reaction mixture at a temperature of about 15 to 40° C.

The last step is the recovery of the polymer-coated, i.e., stabilized, complex from the reaction mixture. The stabilized complex may be recovered from the reaction mixture by freeze-drying or by adding a water-miscible solvent, e.g., acetone, to the reaction mixture to cause the stabilized complex to precipitate out from the reaction mixture. The precipitate is then recovered by conventional filtration methods and it may be dried as described below. Of course, the choice of stabilizing polymer and water-miscible solvent should be such that the polymer will not dissolve in, or otherwise react with, the solvent.

The complex of the invention is preferably recovered by removal of water from the reaction mixture by freeze-drying, a well-known technique for removing water from compositions. Although freeze-drying is a time-consuming process, (a reaction mixture containing one liter of water will typically require 30-36 hours to remove about 97% of the water), it is preferred since the formation of decomposition products resulting from heating the reaction mixture or adding solvents to the reaction mixture can be avoided.

The freeze-drying process will generally be carried out at a reduced pressure and reduced temperature, e.g., a pressure of not greater than 500 milliTorre, preferably 300 to 100 milliTorre and at a temperature of about −60 to about −20° C., preferably −50 to −40° C., The endpoint of the completion of the freeze-drying process may be determined by condensing and measuring the quantity of water removed during the freeze-drying process. The time required for completion of the freeze-drying process will vary depending on factors such as pressure, temperature, quantity of reaction mixture to be free-dried, level of water to be tolerated in the stabilized halide-free glucosamine-drug complex, the thickness and surface area of the reaction mixture in the trays of the freeze-drying equipment, etc.

If the stabilized complex is to be recovered by precipitation from the reaction mixture by addition of a water-miscible solvent such as acetone to the reaction mixture, generally about 2 to about 10 parts of solvent per part of reaction mixture will be required.

After the stabilized complex has been recovered from the reaction mixture, it may be dried by conventional techniques, e.g., a stream of nitrogen, vacuum oven at a temperature of about 30 to about 50° C. for 1 to 10 hours or more, etc.

It should also be noted that the stabilization of the complexes of the invention may provide an additional advantage to warm-blooded vertebrates to whom such complexes are administered. The stabilized, i.e., polymer-coated, versions of the complexes may provide extended release properties, i.e., the glucosamine-therapeutic drug complex may be released within the vertebrate over an extended period of time, thereby possibly resulting in a reduction of the frequency and the amount of the dosage that would otherwise be required to be administered to the vertebrate.

The therapeutic drug that is to be complexed with the halide-free glucosamine may be any therapeutic drug that exhibits an acidic $pK_a$, i.e., a $pK_a$ of less than 7.0. Such drugs will contain one or more acidic functionalities such as a carbonyl moiety, a carboxyl moiety, a sulfoxide moiety, etc. The list of therapeutic drugs that fit such definition is quite voluminous. Suitable therapeutic drugs containing at least one acidic functionality may be found in one or more of the following nonlimiting, representative classes of drugs: α- and β-Adrenergic Agonists; Narcotic and Non-Narcotic Analgesics; Anorexics; Antiallergics; Antianginals; Antiarrhythmics; Antiasthmatics; Antibiotics; Anticoagulants; Anticonvulsants; Antidepressants; Antidiabetics; Antihistaminics; Antihypertensives; Nonsteroidal Anti-Inflammatories; Antimigraines; Antineoplastics; Antiparkinsonians; Antipsychotics; Antispasmodics; Antithrombotics; Antiulceratives; Anxiolytics; Decongestants; Diuretics; Hepatoprotectants; Sedatives, and Vasodilators.

Not every possible therapeutic drug within the foregoing-listed classes will be suitable for preparing a complex with the halide-free glucosamine. Only those therapeutic drugs that are sufficiently acidic in nature to form such a complex with the halide-free glucosamine are suitable. As mentioned above, such therapeutic drugs will have a $pK_a$ of less than 7.0 and will contain at least one acid functionality, e.g. a carbonyl moiety, a carboxyl moiety, a sulfoxide moiety, etc.

Particularly suitable specific drugs within the foregoing classes include: acetaminophen, acetazolamide, ampicillin, ampiroxicam, aspirin, bromfenac, carprofen, celecoxib, cetirizine, chlorothiazide, chlorpropamide, ciprofloxacin, diazepam, diclofenac, ethacrynic acid, flufenamic acid, furosemide, ibuprofen, indomethacin, indoprofen, ketoprofen, levodopa, meclofenamic acid, methotrexate, methyldopa, naproxen, orazamide, penicillamine, pentobarbital, phenobarbital, phenytoin, piroxicam, propylthiouracil, protoporphyrin IX, rofecoxib, salicyclic acid, sulfadiazine, sulfapyridine, sulindac, theophylline, thioctic acid, timonacic, tiopronin, tolbutamide, tolfenamic acid, warfarin, tolmetin, zaltoprofen, and mixtures thereof and the like.

The following nonlimiting examples shall serve to illustrate the preferred embodiments of the invention. Unless otherwise indicated, all parts and percentages are on a weight basis.

EXAMPLE 1

A reaction vessel was equipped with a stirrer and a nitrogen blanket. To the reaction vessel were added 4.1 g (0.02 mole) of ibuprofen and 200 cc of pharmaceutical grade methanol. The mixture was stirred to obtain a solution and thereafter, 3.58 g (0.02 mole) of halide-free glucosamine were added to the reaction mixture. The reaction mixture was then stirred for 1 hour at 25-30° C., resulting in a clear solution. The methanol was stripped off from the reaction mixture using a rotary evaporator at a temperature of 50° C. The resultant glucosamine-ibuprofen complex weighed 7 g.

EXAMPLE 2

A reaction vessel was set up with a stirrer and a warm water bath. Into the reaction vessel were added 1.79 g (0.01 mole) of halide-free glucosamine and the mixture was stirred at 25-35° C. to obtain a clear solution. Thereafter, 3.57 g (0.01 mole) of indomethacin were added and the reaction mixture was stirred for 1 hour at 35-45° C. The reaction mixture was then freeze-dried at a pressure of about 200 milliTorre and a temperature of about −45° C. 3.8 g of a light yellow powder consisting of the glucosamine-indomethacin complex were obtained.

EXAMPLE 3

Example 2 was repeated using 8.6 g (0.05 mole) of halide-free glucosamine, 150 cc of purified water and 7.54 g (0.05 mole) of acetaminophen. 15 g of a white powder consisting of the glucosamine-acetaminophen complex were obtained.

EXAMPLE 4

Example 2 was repeated using 9.0 g (slight excess above 0.05 mole) of halide-free glucosamine, 150 cc of purified water and 9 g (0.05 mole) of acetylsalicyclic acid. 17.4 g of a white solid consisting of the glucosamine-acetylsalicyclic acid complex were obtained.

EXAMPLE 5

Example 2 was repeated using 1.79 g (0.01 mole) of halide-free glucosamine, 100 cc of purified water and 2.3 g (0.01 mole) of naproxen. 3.8 g of a white product consisting of the glucosamine-naproxen complex were obtained.

EXAMPLE 6

Example 2 was repeated using 1.79 g (0.01 mole) of halide-free glucosamine, 100 cc of purified water and 2.96 g (0.01 mole) of diclofenac. 4.0 g of an off-white powder consisting of the glucosamine-diclofenac complex were obtained.

EXAMPLE 7

Example 2 was repeated using 1.79 g (0.01 mole) of halide-free glucosamine, 50 cc of purified water and 0.28 g (0.01 mole) of diazepam. 0.43 g of a white solid consisting of the glucosamine-diazepam complex was obtained.

EXAMPLE 8

Example 1 was repeated using 3.6 g (0.02 mole) of halide-free glucosamine, 300 cc of pharmaceutical grade methanol and 5.04 g (0.02 mole) of phenytoin. 8 g (92% yield) of a white solid consisting of the glucosamine-phenytoin complex were obtained.

What is claimed is:

1. A complex of (a) glucosamine having a purity of at least 99 wt. % and a maximum halide content of about 0.01 wt. %, and (b) a therapeutic drug having a $pK_a$ of less than 7.0.

2. The complex of claim 1 further comprising a coating of a pharmaceutically acceptable polymer.

3. The complex of claim 2 wherein the polymer comprises a water-soluble, water-dispersible and/or a water-swellable homopolymer and/or copolymer.

4. The complex of claim 2 wherein the polymer is selected from the group consisting of carboxypolymethylene homopolymers and copolymers; polyethylene glycol homopolymers and copolymers; polypropylene glycol homopolymers and copolymers; ethylcellulose; povidone homopolymers and copolymers; polyacrylic acid homopolymers and copolymers; polyacrylamide homopolymers and copolymers; polysaccharides; and mixtures of two or more of the foregoing polymers.

5. The complex of claim 2 wherein the polymer is present in an amount of about 2 to about 70 parts by weight, per part of the complex.

6. The complex of claim 1 wherein the therapeutic drug is selected from the group consisting of the classes of α- and β-Adrenergic Agonists; Narcotic and Non-Narcotic Analgesics; Anorexics; Antiallergics; Antianginals; Antiarrhythmics; Antiasthmatics; Antibiotics; Anticoagulants; Anticonvulsants; Antidepressants; Antidiabetics; Antihistaminics; Antihypertensives; Nonsteroidal Anti-Inflammatories; Antimigraines; Antineoplastics; Antiparkinsonians; Antipsychotics; Antipyretics; Antispasmodics; Antithrombotics; Antiulceratives; Anxiolytics; Decongestants; Diuretics; Hepatoprotectants; Sedatives; and Vasodilators.

7. The complex of claim 6 wherein the drug is selected from the group consisting of acetaminophen, acetazolamide, ampicillin, ampiroxicam, aspirin, bromfenac, carprofen, celecoxib, cetirizine, chlorothiazide, chlorpropamide, ciprofloxacin, diazepam, diclofenac, ethacrynic acid, flufenamic acid, furosemide, ibuprofen, indomethacin, indoprofen, ketoprofen, levodopa, meclofenamic acid, methotrexate, methyldopa, naproxen, orazamide, penicillamine, pentobarbital, phenobarbital, phenytoin, piroxicam, propylthiouracil, protoprophyrin IX, rofecoxib, salicyclic acid, sulfadiazine, sulfapyridine, sulindac, theophylline, thioctic acid, timonacic, tiopronin, tolbutamide, tolfenamic acid, warfarin, tolmetin, zaltoprofen, and mixtures thereof.

8. The complex of claim 1 wherein the glucosamine and the drug are present in the complex in an amount of about 1 to about 15 moles of glucosamine per mole of the drug.

9. A coated complex of (a) glucosamine having a purity of at least 99 wt. % and a maximum halide content of about 0.01 wt. %, and (b) a therapeutic drug having a $pK_a$ of less than 7, said coating comprising a pharmaceutically acceptable polymer such that the coated complex will be stable upon exposure to the atmosphere or ambient temperature.

10. The coated complex of claim 9 wherein the pharmaceutically acceptable polymer comprises a water-soluble, water-dispersible and/or a water-swellable homopolymer and/or copolymer.

11. The coated complex of claim 9 wherein the pharmaceutically acceptable polymer is selected from the group consisting of carboxypolymethylene homopolymers and copolymers; polyethylene glycol homopolymers and copolymers; polypropylene glycol homopolymers and copolymers; ethylcellulose; povidone homopolymers and copolymers; polyacrylic acid homopolymers and copolymers; polyacrylamide homopolymers and copolymers; polysaccharides; and mixtures of two or more of the foregoing polymers.

12. The coated complex of claim 9 wherein the pharmaceutically acceptable polymer is present in the complex in an amount of about 2 to about 70 parts by weight, per part of the complex.

13. The coated complex of claim 9 wherein the therapeutic drug is selected from the group consisting of the classes of α- and β-Adrenergic Agonists; Narcotic and Non-Narcotic Analgesics; Anorexics; Antiallergics; Antianginals; Antiarrhythmics; Antiasthmatics; Antibiotics; Anticoagulants; Anticonvulsants; Antidepressants; Antidiabetics; Antihistaminics; Antihypertensives; Nonsteroidal Anti-Inflammatories; Antimigraines; Antineoplastics; Antiparkinsonians; Antipsychotics; Antipyretics; Antispasmodics; Antithrombotics; Antiulceratives; Anxiolytics; Decongestants; Diuretics; Hepatoprotectants; Sedatives; and Vasodilators.

14. The coated complex of claim 13 wherein the drug is selected from the group consisting of acetaminophen, acetazolamide, ampicillin, ampiroxicam, aspirin, bromfenac, carprofen, celecoxib, cetirizine, chlorothiazide, chlorpropamide, ciprofloxacin, diazepam, diclofenac, ethacrynic acid, flufenamic acid, furosemide, ibuprofen, indomethacin, indoprofen, ketoprofen, levodopa, meclofenamic acid, methotrexate, methyldopa, naproxen, orazamide, penicillamine, pentobarbital, phenobarbital, phenytoin, piroxicam, propylthiouracil, protoprophyrin IX, rofecoxib, salicyclic acid, sulfadiazine, sulfapyridine, sulindac, theophylline, thioctic acid, timonacic, tiopronin, tolbutamide, tolfenamic acid, warfarin, tolmetin, zaltoprofen, and mixtures thereof.

15. The coated complex of claim 9 wherein the glucosamine is present in the complex in an amount of about 1 to about 15 moles of glucosamine per mole of the drug.

16. A method for preparing a complex of (a) glucosamine having a purity of at least about 99 wt. % and a maximum halide content of about 0.01 wt. %, and (b) a therapeutic drug having a $pK_a$ comprising the steps of:
   (i) dissolving the glucosamine in water;
   (ii) adding the therapeutic drug to the aqueous solution resulting from step (i); and
   (iii) recovering the complex from the reaction mixture produced in step (ii).

17. The method of claim 15 further comprising adding a pharmaceutically acceptable polymer to the reaction mixture resulting from step (i) prior to carrying out step (ii) such that a stabilized complex is recovered in step (iii).

18. The method of claim 17 wherein the pharmaceutically acceptable polymer comprises a water-soluble, water-dispersible and/or a water-swellable homopolymer and/or copolymer.

19. The method of claim 17 wherein the pharmaceutically acceptable polymer is selected from the group consisting of carboxypolymethylene homopolymers and copolymers; polyethylene glycol homopolymers and copolymers; polypropylene glycol homopolymers and copolymers; ethylcellulose; povidone homopolymers and copolymers; polyacrylic acid homopolymers and copolymers; polyacrylamide homopolymers and copolymers; polysaccharides; and mixtures of two or more of the foregoing polymers.

20. The method of claim 17 wherein the pharmaceutically acceptable polymer is added to the reaction mixture in an amount of about 2 to about 70 parts by weight, per part of the complex.

21. The method of claim 16 wherein step (c) is carried out by adding a water-miscible solvent to the reaction mixture so as to precipitate the complex therefrom.

22. The method of claim 16 wherein step (iii) is carried out by freeze-drying.

23. The method of claim 16 wherein the glucosamine is employed in an amount of about 1 to about 15 moles of glucosamine per mole of the drug.

* * * * *